(12) United States Patent
Poquet et al.

(10) Patent No.: US 10,057,464 B2
(45) Date of Patent: Aug. 21, 2018

(54) ASSISTIVE DEVICE FOR POSITIONING A MEDICAL INSTRUMENT RELATIVE TO AN INTERNAL ORGAN OF A PATIENT

(71) Applicants: UNIVERSITE PIERRE ET MARIE CURIE (PARIS 6), Paris (FR); KOELIS, Grenoble (FR); CENTRE NATIONAL DE LA RECHERCHE SCIENTIFIQUE, Paris (FR)

(72) Inventors: Cecile Poquet, Ivry-sur-Seine (FR); Pierre Mozer, Vincennes (FR); Michael Baumann, Grenoble (FR); Marie-Aude Vitrani, Paris (FR); Guillaume Morel, Paris (FR); Antoine Leroy, Meylan (FR); Patrick Henry, Bios-Colombes (FR); Gregoire Coffin, Paris (FR)

(73) Assignees: SORBONNE UNIVERSITE, Paris (FR); KOELIS, Grenoble (FR); CENTRE NATIONAL DE LA RECHERCHE SCIENTIFIQUE, Paris (FR)

( * ) Notice: Subject to any disclaimer, the term of this patent is extended or adjusted under 35 U.S.C. 154(b) by 379 days.

(21) Appl. No.: 14/362,951

(22) PCT Filed: Dec. 6, 2012

(86) PCT No.: PCT/EP2012/074711
§ 371 (c)(1),
(2) Date: Jun. 5, 2014

(87) PCT Pub. No.: WO2013/083731
PCT Pub. Date: Jun. 13, 2013

(65) Prior Publication Data
US 2014/0354792 A1    Dec. 4, 2014

(30) Foreign Application Priority Data

Dec. 6, 2011 (FR) ..................... 11 61217

(51) Int. Cl.
*H04N 5/225* (2006.01)
*G06T 7/00* (2017.01)
(Continued)

(52) U.S. Cl.
CPC ....... *H04N 5/2251* (2013.01); *A61B 10/0241* (2013.01); *A61B 34/76* (2016.02); *G06T 7/0012* (2013.01); *A61B 2090/378* (2016.02)

(58) Field of Classification Search
None
See application file for complete search history.

(56) References Cited

U.S. PATENT DOCUMENTS

| 6,785,572 B2 * | 8/2004 | Yanof | A61B 34/70 600/411 |
| 2005/0159676 A1 * | 7/2005 | Taylor | A61B 10/0275 600/567 |

(Continued)

FOREIGN PATENT DOCUMENTS

| WO | 2006/091494 A1 | 8/2006 | |
| WO | WO 2006091494 A1 * | 8/2006 | ............. A61B 90/36 |

OTHER PUBLICATIONS

Michael A. Greminger, et al., "Vision-Based Force Measurement", IEEE Transactions on Pattern Analysis and Machine Intelligence, Mar. 2004, pp. 290-298, vol. 26, No. 3.
(Continued)

*Primary Examiner* — Edemio Navas, Jr.
(74) *Attorney, Agent, or Firm* — Sughrue Mion, PLLC

(57) ABSTRACT

The invention relates to an assistive device for positioning a medical instrument (2) inserted into a natural duct (100) or an artificial duct of a patient relative to an internal organ (P)
(Continued)

of a patient, wherein the device comprises a support (1) that is to be inserted at least in part into the body of the patient and supports the medical instrument, means for moving the support, wherein said movement means comprise an articulated arm (9) that includes a plurality of degrees of freedom for moving a proximal end (1a) of the support, means for acquiring images of the internal organ for positioning the medical instrument relative to the internal organ, wherein the image acquisition means comprise a probe (5) supported by the support such that the medical instrument and the probe are rigidly connected, and a control unit (10) for controlling the movement means, which is connected to the image acquisition means and comprises image analyzing means (11) for generating control commands for the articulated arm in order to control at least one movement of the medical instrument relative to the internal organ. The invention further relates to a method for controlling such a device.

19 Claims, 1 Drawing Sheet

(51) Int. Cl.
 *A61B 10/02* (2006.01)
 *A61B 34/00* (2016.01)
 *A61B 90/00* (2016.01)

(56) References Cited

U.S. PATENT DOCUMENTS

| | | |
|---|---|---|
| 2006/0207978 A1 | 9/2006 | Rizun et al. |
| 2007/0167698 A1* | 7/2007 | Lloyd .................. A61B 6/4441 600/407 |
| 2009/0118640 A1 | 5/2009 | Miller et al. |
| 2009/0247859 A1* | 10/2009 | Daum .................... A61B 90/10 600/411 |
| 2010/0056900 A1* | 3/2010 | Whitcomb ............. A61B 5/055 600/414 |

OTHER PUBLICATIONS

International Search Report of PCT/EP2012/074711, dated Feb. 21, 2013.

* cited by examiner

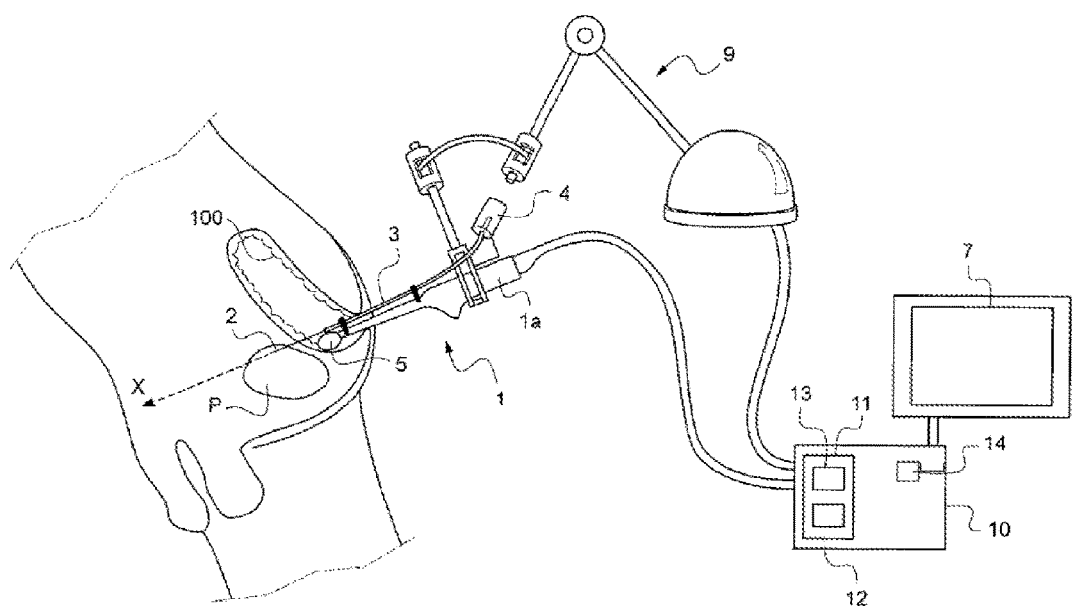

ASSISTIVE DEVICE FOR POSITIONING A MEDICAL INSTRUMENT RELATIVE TO AN INTERNAL ORGAN OF A PATIENT

CROSS REFERENCE TO RELATED APPLICATIONS

This application is a National Stage of International Application No. PCT/EP2012/074711 filed Dec. 6, 2012, claiming priority based on French Patent Application No. 11 61217, filed Dec. 6, 2011, the contents of all of which are incorporated herein by reference in their entirety.

The invention relates to an assistive device for positioning a medical instrument relative to an internal organ of a patient. The invention further relates to a method for controlling such a device.

More specifically, the invention relates to an assistive device which is used for positioning a medical instrument relative to an internal organ of a patient and which has a control unit for controlling means of movement of said medical instrument, the control unit being connected to image acquisition means for the internal organ and having image analysis means for generating control commands for the means of movement.

TECHNOLOGICAL BACKGROUND OF THE INVENTION

"Open" surgery is known to be very demanding for patients. For this reason, practitioners are increasingly using minimally invasive operations in which medical instruments are inserted into a natural duct of the patient (vagina, rectum, auditory meatus, etc.) or into an artificial duct connected to the body of the patient (cannula, artificial vein, trocar, etc.).

In urology, it is known to perform a prostate biopsy in order to screen for possible prostate cancer. This involves taking tissue samples from within the prostate, said samples then being analyzed in a laboratory in order to detect the presence of any cancer cells. For this, the patient lies on his side. A medical instrument comprising an ultrasound sensor and a needle guide with a biopsy needle is then inserted into the natural duct formed by the rectum. Using the medical instrument, the surgeon perforates the colon wall in order to access the prostate and thus take tissue samples.

To perform the biopsy, the only images the surgeon can use are two-dimensional ones taken in real time by the ultrasound sensor. The surgeon therefore has to imagine a three-dimensional representation of the prostate in order to take the samples distributed regularly within the volume of the prostate. This therefore requires very great dexterity on the part of the surgeon.

Furthermore, the prostate is an extremely soft organ, such that simple contact by the needle, without the latter being driven into the prostate, is enough to deform said prostate. Thus, even if the surgeon thinks the samples have been taken correctly, it is possible that he has not pierced the prostate at exactly the required spot. There is then a risk that the samples have not been taken uniformly from the prostate.

Devices have recently appeared to help the surgeon perform the various types of aspiration very precisely.

New devices comprise probes that can provide three-dimensional images of the prostate. The operating principle of said planning is to plan theoretical positions for the aspirations and to study the deformation of the prostate during the biopsy. The theoretical aspiration plan is then modified depending on the study of deformation of the prostate so that the aspirations can be done at the right places. However, the correct positioning according to the new plan remains entirely dependent on the skill of the surgeon.

What is more, it is possible that the patient is not under local anesthesia and/or is not immobilized. This means that the patient, and thus all the tissues of the natural or artificial duct with which the medical instrument can come into contact, can move during the operation.

To assist the surgeon, devices for guiding a medical instrument are known comprising an articulated arm for moving a proximal end of the medical instrument. The surgeon can then control the articulated arm so that it blocks the medical instrument in a given position. However, guiding devices of this kind consider positions of the medical instrument that are defined in a reference system fixed with respect to the examination room in which the patient is placed.

However, the patient and/or his prostate can move, and this has two major implications.

Firstly, the prostate is not fixed with respect to the reference system in which the control of the position of the articulated arm is defined. It can therefore happen that the prostate has changed position between the moment when the desired position of the medical instrument is given to the articulated arm and the moment when this position is reached by the medical instrument. Thus, the target reached by the medical instrument may be correct from the point of view of the articulated arm in the fixed reference system but wrong from the point of view of the prostate: the puncture is not made in the intended area of the prostate.

Secondly, the point of entry of the medical instrument into the body of the patient moves with the patient. Thus, the articulated arm may oppose any movements of the patient, which can be uncomfortable for the patient and even damage some of the patient's tissues.

During the intervention, the point of entry of the medical instrument into the patient exposes the medical instrument to "parasite" forces which hide the tactile information useful to the surgeon, namely the stresses of interaction between the medical instrument and the targeted organ. For this reason, the surgeon is not fully aware of the stresses applied to the prostate and may cause considerable deformation and/or considerable movement of the prostate without even knowing.

OBJECT OF THE INVENTION

It is an aim of the invention to propose an assistive device which is used for positioning a medical instrument, inserted into a natural duct or an artificial duct of a patient, relative to an internal organ, and which at least partly avoids the aforementioned disadvantages.

BRIEF DESCRIPTION OF THE INVENTION

With a view to achieving this aim, the invention proposes an assistive device for positioning a medical instrument, inserted into a natural duct or an artificial duct of a patient, relative to an internal organ of a patient, the device having:
  a support which is dedicated to be inserted at least in part into the body of the patient and which supports the medical instrument;
  movement means for moving the support, said movement means having an articulated arm which has a plurality of degrees of freedom for moving a proximal end of the support;

image acquisition means for acquiring images of the internal organ in order to position the medical instrument relative to the internal organ, the image acquisition means having a probe carried by the support, such that the medical instrument and the probe are rigidly connected;

a control unit which controls the movement means, is connected to the image acquisition means and has image analysis means for generating control commands intended for the articulated arm in order to control at least one movement of the medical instrument relative to the internal organ, the analysis means having means for estimating a distance between the probe and the internal organ in order to brake a movement of the articulated arm as a function of said distance.

Thus, the support carries both the probe and also the medical instrument, such that the relative positioning of the probe with respect to the medical instrument is known. The images taken by the probe are representative of a position of the probe with respect to the internal organ and therefore also directly representative of the position of the medical instrument with respect to the internal organ. It is thus possible to estimate in real time the position of the medical instrument with respect to the internal organ, without retiming.

The device also has an articulated arm having a plurality of degrees of freedom in order to move the proximal end of the support by generating forces at this end. On account of the insertion of the medical instrument into the patient, the position of the medical instrument is well defined and can be modified by the articulated arm being able to act on the position of the proximal end of the support and therefore of the medical instrument.

The articulated arm is not alone in acting on the position of the medical instrument: a surgeon also manipulates the support and therefore the medical instrument. It is thus the combination of the forces exerted on the support by the surgeon and also by the articulated arm that will determine the movements and the position of the medical instrument.

Thus, the support is manipulated both by the surgeon and also by the articulated arm, by which means it is possible to act on the position of the medical instrument and on the tactile feel of the practitioner.

Indeed, the generation of forces by the articulated arm does not have the aim of manipulating the medical instrument alone, but of modifying the feel of the surgeon and therefore his maneuvers, especially for example by allowing him to feel forces that are representative of the interaction between the medical instrument and the organ or by modifying his maneuver in such a way as to position the medical instrument in the target position.

Furthermore, by virtue of the means of estimation of the distance between the probe and the internal organ, the control unit can generate control commands for providing resistance to the movement of the medical instrument as a function of said distance, such that the support is increasingly braked as the needle approaches the prostate.

Once again, the device according to the invention assists the surgeon in the procedure that he has to perform on the internal organ, which ensures, for example, that the surgeon does not press the medical instrument too firmly or too rapidly on the internal organ.

The device according to the invention is particularly useful for bringing a medical instrument toward a soft organ such as the prostate, of which the deformation is extremely frequent.

This is because the images from the probe allow the deformation of the prostate to be taken into account in order to position the medical instrument correctly with respect to the prostate despite the deformation of the latter. It is thus possible to perform a biopsy at a very precise location.

In addition, with the devices of the prior art, it has been found that because of the considerable deformability of the prostate, most surgeons sometimes have the impression that they have not yet reached the prostate P when in fact they are already compressing it. By virtue of the device according to the invention, the surgeon can be guided as far as the prostate in such a way as to rest the medical instrument on the latter without compressing it, which means that the medical instrument can be positioned much better relative to the prostate before a medical procedure is performed on said prostate.

The invention further relates to a method for controlling such a device, which method comprises the steps of:
acquiring at least one image of the internal organ using the acquisition means;
analyzing said image using the image analysis means;
generating a control command for the articulated arm as a function of the analysis of this image.

The invention further relates to a method for controlling such a device, which method comprises the steps of:
acquiring at least one reference image of the internal organ,
acquiring at least a first image of the internal organ using the image acquisition means,
using the means for estimating to calculate, by comparison between the image and the reference image, the axis of principal deformation of the internal organ, and also the value of the deformation of the organ on this axis,
using the means for estimating to transpose the direction of principal deformation and the value of this principal deformation into a reference frame associated with the articulated arm,
determining, from the indication of the direction and the value of the principal deformation, the distance between the medical instrument and the internal organ,
generating a control command for the articulated arm in accordance with the deformation of this distance.

BRIEF DESCRIPTION OF THE DRAWINGS

The invention will be better understood in light of the following description of a specific non-limiting embodiment of the invention and by reference to the single FIGURE, which is a schematic view of an assistive device according to the invention, with part of the body of a patient being shown.

DETAILED DESCRIPTION OF THE INVENTION

The assistive device according to the invention for positioning a medical instrument relative to an internal organ of a patient is here intended to bring a medical instrument into proximity with a prostate. This use is of course-non-limiting, and the device according to the invention will be able to be used to bring a medical instrument into proximity with any internal organ, for example a bladder.

Referring to FIG. 1, the device comprises a support 1 with a needle holder 3 which receives a needle 2 for performing a biopsy on a prostate P of a patient. The support 1 additionally has actuation means 4 for the needle holder 3 in order to insert the needle 2 and withdraw it from the prostate P along a defined working axis X.

The support 1 is intended to be introduced at least in part into the body of the patient such that the needle 2 is close to the prostate P. For this purpose, the device has movement means for moving the support 1. Said means have an articulated arm 9 with a plurality of degrees of freedom for moving a proximal end 1a of the support. Proximal end means the end opposite the one introduced into the body of the patient.

The device also has means for acquiring images of the prostate P in order to position the needle 2 relative to the prostate P. The image acquisition means have an ultrasound probe 5. According to the invention, the probe 5 is carried by the support 1, such that the probe 5 and the needle holder 3 and the needle 2 are rigidly connected and are introduced together into the rectum 100.

Here, the support 1 is introduced via the natural duct formed by the rectum 100, by passing it through the anus until the probe 5 comes into contact with the rectal wall opposite the prostate P, and, during the biopsy, the needle 2 is inserted into the prostate P through said rectal wall.

Thus, images taken by the probe 5 are representative of the position of the support 1 with respect to the prostate P. As the probe 5 is at a defined distance from the needle 2, of which the needle holder 3 is also rigidly connected to the support 1, these images are also representative of a position of the needle 2 with respect to the prostate P. It is thus possible to determine in real time the position of the needle 2 with respect to the prostate P, which greatly facilitates the work of a practitioner. It should be noted that the rectal wall is very thin, and therefore it does not impede the acquisition of images of the prostate P by the probe 5.

The device according to the invention additionally has a control unit 10 which controls the movement means, in particular the articulated arm 9, and is connected to the image acquisition means, in particular the probe 5. The control unit 10 has analysis means 11 for analyzing said images, in order to generate control commands for the articulated arm 9 and thus control at least one movement of the needle 2 relative to the prostate P.

The control unit 10 thus positions the needle 2 relative to the prostate P by way of the articulated arm 9, using the images from the probe 5. In addition, since no registration is necessary, the control unit 10 can adjust the control commands in real time in order to correctly position the needle 2 with respect to the prostate P when the latter has been deformed or has moved.

Thus, when the support 1 and the movement means are blocked and the needle 2 rests against the prostate P, the analysis means 11 can deduce from the images of the prostate P whether the prostate P has moved relative to the probe 5. If such is the case, it is then necessary to readjust the position of the needle 2 with respect to the prostate P. The control unit 10 thus permanently ensures a precise placement of the needle 2 with respect to the prostate P.

The inventors noticed that some practitioners tended to press the support 1 too firmly against the prostate P. Indeed, because of the lack of visual contact and the considerable deformability of the prostate, practitioners sometimes have the impression that they have not yet reached the prostate P when in fact they are already compressing it.

According to the invention, the analysis means 11 therefore have means 12 for estimating a distance between the probe 5 and the rectal wall that is to be pierced in order to reach the prostate P. Said means of estimation 12 estimate this distance in real time by analyzing the images from the probe 5. The control unit 10 then generates control commands for providing resistance to the movement of the support 1 as a function of said distance, such that the support 1 is increasingly braked as the needle 2 approaches the prostate P.

The practitioner manipulating the device according to the invention, together with the articulated arm 9, senses more and more resistance on the part of the articulated arm 9 and can thus more easily estimate the distance from the prostate P. Force feedback is thus achieved artificially. The force feedback is obtained advantageously without a force sensor.

According to a particular embodiment, the control unit 10 orders braking of the articulated arm 9 as follows.

In an initialization sequence, during a first step, the acquisition means acquire a first image called the reference image.

Said reference image is then sent to the control unit 10. The reference image is, for example, a general image of the prostate P or an image of a particular area of the prostate P. The reference image is, for example, two-dimensional or three-dimensional. As a variant, the reference image is not acquired by the acquisition means but is instead acquired by means of other medical analyses (such as magnetic resonance imaging) and supplied to the control unit 10.

In a sequence of movement of the medical instrument, the acquisition means acquire at least one image and send it to the control unit 10.

By comparison between the image and the reference image, the means of estimation then calculate the axis of principal deformation (i.e. the direction of principal deformation) of the prostate P, and also the value of the deformation of the prostate P on this axis.

The means of estimation then transpose the direction of principal deformation and the value of this principal deformation into a reference frame associated with the articulated arm 9, the position of the probe 5 relative to the articulated arm 9 being known, as has already been seen.

Thereafter, proceeding from the indication of the direction and the value of the principal deformation in the reference frame of the articulated arm 9, the means of estimation determine the distance between the medical instrument 2 (and therefore the probe 5) and the prostate P.

The control unit 10 then manages the articulated arm 9 in such a way that the movements of the medical instrument 2 and of the probe 5 are braked in proportion to the distance between the medical instrument 2 and the prostate P.

The analysis means preferably have means 13 for estimating a deformation of the prostate P when the probe 5 is already in contact with the prostate through the rectal wall. The means of estimation 13 of a deformation estimate this deformation in real time by analyzing the images from the probe 5. For example, the means of estimation 13 of a deformation have means of estimation 15 of a crushing distance of the prostate P by the probe 5. The control unit 10 then generates control commands for providing resistance to the movement of the articulated arm 9 as a function of said deformation, such that the articulated arm 9 is braked more and more as the needle 2 engages in the prostate P and thus deforms the prostate. An artificial stiffness is thus created which helps the practitioner in his maneuvers. In particular, this ensures that the practitioner does not compress the prostate P too much.

For example, it is possible to control the articulated arm with respect to the deformation of the prostate P, for example by estimating the forces generated by the articulated arm on the prostate P using any logic formula (proportionality relationship, for example, with or without damping, reproduction of the law of behavior of the organ, etc.).

According to a particular embodiment, proceeding from the deformation of the prostate P, whether or not the instrument is in contact with the prostate P, it is possible to estimate the distance between a particular area to be reached on the prostate P (for example in order to perform an aspiration in this area) and the medical instrument 2. Indeed, if a particular area of the prostate (called the target) is defined and input in the control unit 10, the control unit 10 uses an image acquired by the acquisition means to calculate the direction in which the medical instrument 2 has to move in order to reach said target, and the distance separating the medical instrument 2 and said target in this direction. With the medical instrument 2 and therefore the probe 5 having a known position with respect to the articulated arm 9, the aforementioned distance and direction can be expressed in a reference frame associated with the articulated arm 9.

The control unit 10 can then generate control commands for the articulated arm, for example such that the articulated arm 9 provides resistance if the practitioner tends to move the medical instrument 2 away from the target or, conversely, such that the articulated arm 9 guides the movement of the practitioner in the correct direction.

According to a preferred embodiment, the control unit 10 has selection means 14 for selecting a mode of manipulation of the articulated arm 9. According to a first mode of manipulation of the articulated arm 9, the articulated arm 9 alone provides the movement of the support 1. According to a second mode of manipulation of the articulated arm 9, the practitioner also moves the support 1 in conjunction with the articulated arm 9, for example at the proximal end 1a of the support 1. For this purpose, the proximal end 1a is preferably shaped as a handle. The articulated arm 9 is thus able to be co-manipulated. According to a third mode of manipulation of the articulated arm 9, the practitioner can move the support 1 only in some degrees of freedom. The articulated arm 9 is then partially able to be co-manipulated.

The practitioner can thus choose to what extent he wishes to be assisted by the articulated arm 9. The device according to the invention thus adapts to the needs of the practitioner by being able to be co-manipulated.

The device according to the invention can help the practitioner position the needle 2 precisely with respect to the prostate P and can also improve a tactile feel of the practitioner.

The articulated arm 9 is therefore not alone in acting on the position of the needle 2: the practitioner also manipulates the support 1 and therefore, indirectly, the needle 2. It is thus the combination of the forces exerted on the support by the practitioner and also by the articulated arm 9 that will determine the movements and the position of the needle.

Thus, the support 1 is manipulated both by the practitioner and also by the articulated arm 9, by which means it is possible to act on the position of the needle and on the tactile feel of the practitioner.

Indeed, the generation of forces by the articulated arm 9 does not have the aim of manipulating the needle alone, but of modifying the feel of the practitioner and therefore his maneuvers, especially for example by allowing him to feel forces that are representative of the interaction between the needle 2 and the prostate P or by modifying his maneuver in such a way as to position the needle in the target position.

According to a preferred embodiment, the movement means are connected to the proximal end 1a of the support 1 by a connection of the ball-joint type R.

It is possible that the patient is not under local anesthesia and/or is not immobilized. Thus, the anus into which the needle 2 is introduced is not necessarily fixed. The ball-joint connection R advantageously prevents the movement means from opposing natural movements of the patient. The device according to the invention thus respects the anatomy of the patient.

The device according to the invention has a display screen 7 for the images taken by the probe 5. The display screen is connected to the control unit 10. Thus, a practitioner can have visual feedback and can estimate the distance of the needle 2 relative to the prostate P.

The device according to the invention preferably has means for blocking the support 1. Thus, once the needle 2 has been correctly positioned with respect to the prostate P, the practitioner can block a movement of the support 1 and of the articulated arm 9 before inserting the needle 2 into the prostate P.

Of course, the invention is not limited to the described embodiment, and variations can be made thereto without departing from the scope of the invention as defined by the claims.

The device will be able to bring any other medical instrument close to an internal organ, not just a needle holder carrying a needle. Moreover, the device will allow a medical instrument to be brought close to any other organ, not just a prostate. In particular, the device is not exclusively intended for the male genital system. Moreover, although the target organ is reached here by introducing the support through a natural duct, namely the rectum, it will be possible to reach the target organ by introducing the support into the body of the patient via an artificial route such as a trocar.

It will be possible for the probe to be other than an ultrasound probe, for example an optical or infrared device.

The movement means will be able to be connected to the proximal end of the support by a connection other than a ball-joint connection, for example a connection of the cardan type.

It will be possible for the control unit to have means for selecting a mode of manipulation of the movement means. In particular, it will be possible for the control unit to have means for selecting a mode of manipulation of the movement means in which the movement means are able to be co-manipulated. It will be possible for the control unit to have means for selecting a mode of manipulation of the movement means in which the movement means are partially able to be co-manipulated.

It will be possible for the articulated arm to be configured in order to allow the proximal end of the support to move in any number of degrees of freedom, provided that it can at least permit a movement of the proximal end of the support inside the body of the patient.

The invention claimed is:

1. An assistive device for positioning a medical instrument (2), inserted into a natural duct (100) or an artificial duct of a patient, relative to an internal organ (P) of a patient, the device having:
   a support (1) which is dedicated to be inserted at least in part into the body of the patient and which supports the medical instrument;
   movement means for moving the support, said movement means having an articulated arm (9) which has a plurality of degrees of freedom for moving a proximal end (1a) of the support, the device structured so that the support is co-manipulated by the articulated arm and an operator of the assistive device, so that a combination of physical forces exerted on the support by the operator and by the articulated arm determine movements and positions of the medical instrument;

image acquisition means for acquiring images of the internal organ in order to position the medical instrument relative to the internal organ, the image acquisition means having a probe (5) carried by the support, such that the medical instrument and the probe are rigidly connected;

a control unit (10) which controls the movement means, is connected to the image acquisition means and has image analysis means (11) for generating control commands for the articulated arm in order to control at least one movement of the medical instrument relative to the internal organ, the analysis means having means (12) for estimating a distance between the probe (5) and the internal organ in order to brake a movement of the articulated arm (9) as a function of said distance; wherein the movement of the articulated arm is increasingly braked as said distance becomes shorter, wherein the braking is a force opposed to operator movement of the medical instrument.

2. The device as claimed in claim 1, in which the analysis means have means (13) for estimating a deformation of the internal organ in order to brake a movement of the articulated arm (9) as a function of said deformation.

3. The device as claimed in claim 1, in which the articulated arm (9) is connected to the proximal end (1a) of the support (3) by a connection of the cardan or ball-joint type.

4. The device as claimed in claim 1, in which the probe (5) is an ultrasound probe.

5. The device as claimed in claim 1, having a display screen (7) for the images taken by the probe (5).

6. The device as claimed in claim 1, in which the medical instrument is a needle (2).

7. A method for controlling an assistive device for positioning a medical instrument, inserted into a natural duct or an artificial duct of a patient, relative to an internal organ of a patient, the method comprising the steps of:
providing the assistive device of claim 1;
acquiring at least one image of the internal organ using the acquisition means (5);
analyzing said image using the image analysis means (11);
generating a control command for the articulated arm (9) as a function of the analysis of the image.

8. A method for controlling an assistive device for positioning a medical instrument, inserted into a natural duct or an artificial duct of a patient, relative to an internal organ of a patient, the method comprising the steps of:
providing the assistive device of claim 2;
acquiring at least one image of the internal organ using the acquisition means (5);
analyzing said image using the image analysis means (11);
generating a control command for the articulated arm (9) as a function of the analysis of the image.

9. A method for controlling an assistive device for positioning a medical instrument, inserted into a natural duct or an artificial duct of a patient, relative to an internal organ of a patient, the method comprising the steps of:
providing the assistive device of claim 3;
acquiring at least one image of the internal organ using the acquisition means (5);
analyzing said image using the image analysis means (11);
generating a control command for the articulated arm (9) as a function of the analysis of the image.

10. A method for controlling an assistive device for positioning a medical instrument, inserted into a natural duct or an artificial duct of a patient, relative to an internal organ of a patient, the method comprising the steps of:
providing the assistive device of claim 4;
acquiring at least one image of the internal organ using the acquisition means (5);
analyzing said image using the image analysis means (11);
generating a control command for the articulated arm (9) as a function of the analysis of the image.

11. A method for controlling an assistive device for positioning a medical instrument, inserted into a natural duct or an artificial duct of a patient, relative to an internal organ of a patient, the method comprising the steps of:
providing the assistive device of claim 5;
acquiring at least one image of the internal organ using the acquisition means (5);
analyzing said image using the image analysis means (11);
generating a control command for the articulated arm (9) as a function of the analysis of the image.

12. A method for controlling an assistive device for positioning a medical instrument, inserted into a natural duct or an artificial duct of a patient, relative to an internal organ of a patient, the method comprising the steps of:
providing the assistive device of claim 4;
acquiring at least one image of the internal organ using the acquisition means (5);
analyzing said image using the image analysis means (11);
generating a control command for the articulated arm (9) as a function of the analysis of the image.

13. An assistive device for positioning a medical instrument, inserted into a natural duct or an artificial duct of a patient, relative to an internal organ of a patient, the device having:
a support which is dedicated to be inserted at least in part into the body of the patient and which supports the medical instrument;
a movement mechanism that moves the support, said movement mechanism having an articulated arm which has a plurality of degrees of freedom for moving a proximal end of the support, the device structured so that the support is co-manipulated by the articulated arm and manually by an operator of the assistive device, so that a combination of physical forces exerted on the support by the operator and by the articulated arm determine movements and positions of the medical instrument;
image acquisition means for acquiring images of the internal organ in order to position the medical instrument relative to the internal organ, the image acquisition means having a probe carried by the support, such that the medical instrument and the probe are rigidly connected;
a control unit which controls the movement mechanism, is connected to the image acquisition means and has image analysis means for generating control commands for the articulated arm in order to control at least one movement of the medical instrument relative to the internal organ, the analysis means having means for estimating a distance between the probe and the internal organ in order to brake a movement of the articulated arm as a function of said distance wherein the analysis means have means for estimating a deformation of the internal organ in order to brake a movement of the articulated arm as a function of said deformation, wherein the analysis means estimates the deformation of the internal organ based on the images acquired by the image acquisition means.

14. An assistive device for positioning a medical instrument (2), inserted into a natural duct (100) or an artificial duct of a patient, relative to an internal organ (P) of a patient, the device having:
   a support (1) which is dedicated to be inserted at least in part into the body of the patient and which supports the medical instrument;
   a movement mechanism that moves the support, said movement mechanism having an articulated arm (9) which has a plurality of degrees of freedom for moving a proximal end (1a) of the support, the device structured so that the support is co-manipulated by the articulated arm and manually by an operator of the assistive device, so that a combination of physical forces exerted on the support by the operator and by the articulated arm determine movements and positions of the medical instrument;
   image acquisition means for acquiring images of the internal organ in order to position the medical instrument relative to the internal organ, the image acquisition means having a probe (5) carried by the support, such that the medical instrument and the probe are rigidly connected;
   a control unit (10) which controls the movement mechanism, is connected to the image acquisition means and is configured to generate control commands for the articulated arm in order to control at least one movement of the medical instrument relative to the internal organ, the control unit (10) being also configured to estimate a distance between the probe (5) and the internal organ in order to brake a movement of the articulated arm (9) as a function of said distance wherein the movement of the articulated arm (9) is increasingly braked as said distance becomes shorter.

15. An assistive device for positioning a medical instrument (2), inserted into a natural duct (100) or an artificial duct of a patient, relative to an internal organ (P) of a patient, the device having:
   a support (1) which is dedicated to be inserted at least in part into the body of the patient and which supports the medical instrument;
   movement means for moving the support, said movement means having an articulated arm (9) which has a plurality of degrees of freedom for moving a proximal end (1a) of the support, the device structured so that the support is co-manipulated by the articulated arm and manually by an operator of the assistive device, so that a combination of physical forces exerted on the support by the operator and by the articulated arm determine movements and positions of the medical instrument;
   image acquisition means for acquiring images of the internal organ in order to position the medical instrument relative to the internal organ, the image acquisition means having a probe (5) carried by the support, such that the medical instrument and the probe are rigidly connected;
   a control unit (10) which controls the movement means, is connected to the image acquisition means and is configured to generate control commands for the articulated arm in order to control at least one movement of the medical instrument relative to the internal organ, the control unit being also configured for estimating a distance between the probe (5) and the internal organ in order to brake a movement of the articulated arm (9) as a function of said distance wherein the control unit being configured for estimating a deformation of the internal organ in order to brake a movement of the articulated arm (9) as a function of said deformation.

16. An assistive device for positioning by an operator a medical instrument (2), inserted into a natural duct (100) or an artificial duct of a patient, relative to a target internal organ (P) of a patient, the device comprising:
   a support (1) which is dedicated to be inserted at least in part into the body of the patient and which supports the medical instrument;
   movement means for moving the support, said movement means having an articulated arm (9) which has a plurality of degrees of freedom for moving a proximal end (1a) of the support;
   image acquisition means for acquiring images of the internal organ in order to position the medical instrument relative to the internal organ, the image acquisition means having a probe (5) carried by the support, such that the medical instrument and the probe are rigidly connected;
   a control unit (10) which controls the movement means, is connected to the image acquisition means and has image analysis means (11) for generating control commands for the articulated arm in order to control at least one movement of the medical instrument relative to the internal organ, the analysis means having means (12) for estimating a distance between the probe (5) and the internal organ in order to brake a movement of the articulated arm (9) as a function of said distance wherein the movement of the articulated arm (9) is increasingly braked as said distance becomes shorter;
   wherein the braking creates an artificial stiffness of the arm in order to aid an operator of the assistive device from causing discomfort to the patient by approaching rapidly or from damaging the target internal organ by excessive compression; and
   wherein the device is arranged so that the support is co-manipulated by the articulated arm and the operator so that a combination of forces exerted on the support by the operator and by the articulated arm determine movements and positions of the medical instrument.

17. The device according to claim 16, wherein braking is a force opposed to the free and manual movement of the medical instrument in order to minimize the force applied to the organ.

18. The device according to claim 16, wherein force feedback is created artificially without a force sensor.

19. The device according to claim 16, wherein the braking modifies a sensation by the operator, thereby assisting the operator in maneuvering the arm.

* * * * *